(12) United States Patent
Schmidt et al.

(10) Patent No.: US 7,825,290 B2
(45) Date of Patent: Nov. 2, 2010

(54) DISPOSABLE ABSORBENT ARTICLES HAVING LOW REWET AND A REDUCED EVAPORATION FROM THE CORE THROUGH THE TOPSHEET

(75) Inventors: Mattias Schmidt, Idstein (DE); Cornelia Sprengard-Eichel, Frankfurt (DE); Bruno Johannes Ehrnsperger, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 175 days.

(21) Appl. No.: 10/323,572

(22) Filed: Dec. 18, 2002

(65) Prior Publication Data

US 2003/0097101 A1   May 22, 2003

Related U.S. Application Data

(63) Continuation of application No. PCT/US00/17083, filed on Jun. 21, 2000.

(51) Int. Cl.
*A61F 13/15*   (2006.01)
*A61F 13/20*   (2006.01)

(52) U.S. Cl. .................. 604/378; 604/383; 604/382

(58) Field of Classification Search ............... 604/367, 604/370, 372, 378–383, 385.01, 358, 358.22–358.24, 604/385.27
See application file for complete search history.

(56) References Cited

U.S. PATENT DOCUMENTS

| | | | |
|---|---|---|---|
| 4,321,924 A * | 3/1982 | Ahr ........................... 604/378 |
| 5,437,653 A | 8/1995 | Gilman et al. |
| 5,728,451 A | 3/1998 | Langley et al. |
| 5,785,697 A | 7/1998 | Trombetta et al. |
| 5,865,823 A | 2/1999 | Curro |
| 6,429,352 B1 * | 8/2002 | Herrlein et al. ............. 604/383 |
| 6,455,753 B1 * | 9/2002 | Glaug et al. ................ 604/383 |

FOREIGN PATENT DOCUMENTS

| EP | 0 749 738 A1 | 12/1996 |
|---|---|---|
| EP | 0 774 242 A1 | 5/1997 |
| EP | 0 797 968 A1 | 10/1997 |
| EP | 0 842 650 A1 | 5/1998 |
| WO | 97/00057 | * 1/1997 |

* cited by examiner

*Primary Examiner*—Michele Kidwell
(74) *Attorney, Agent, or Firm*—John G. Powell; Ken K. Patel

(57) ABSTRACT

Absorbent article, wherein a liquid acquisition/distribution region comprises an evaporation barrier, such as an apertured film and thus exhibits reduced evaporation away from the article in the direction towards the wearer.

8 Claims, 4 Drawing Sheets

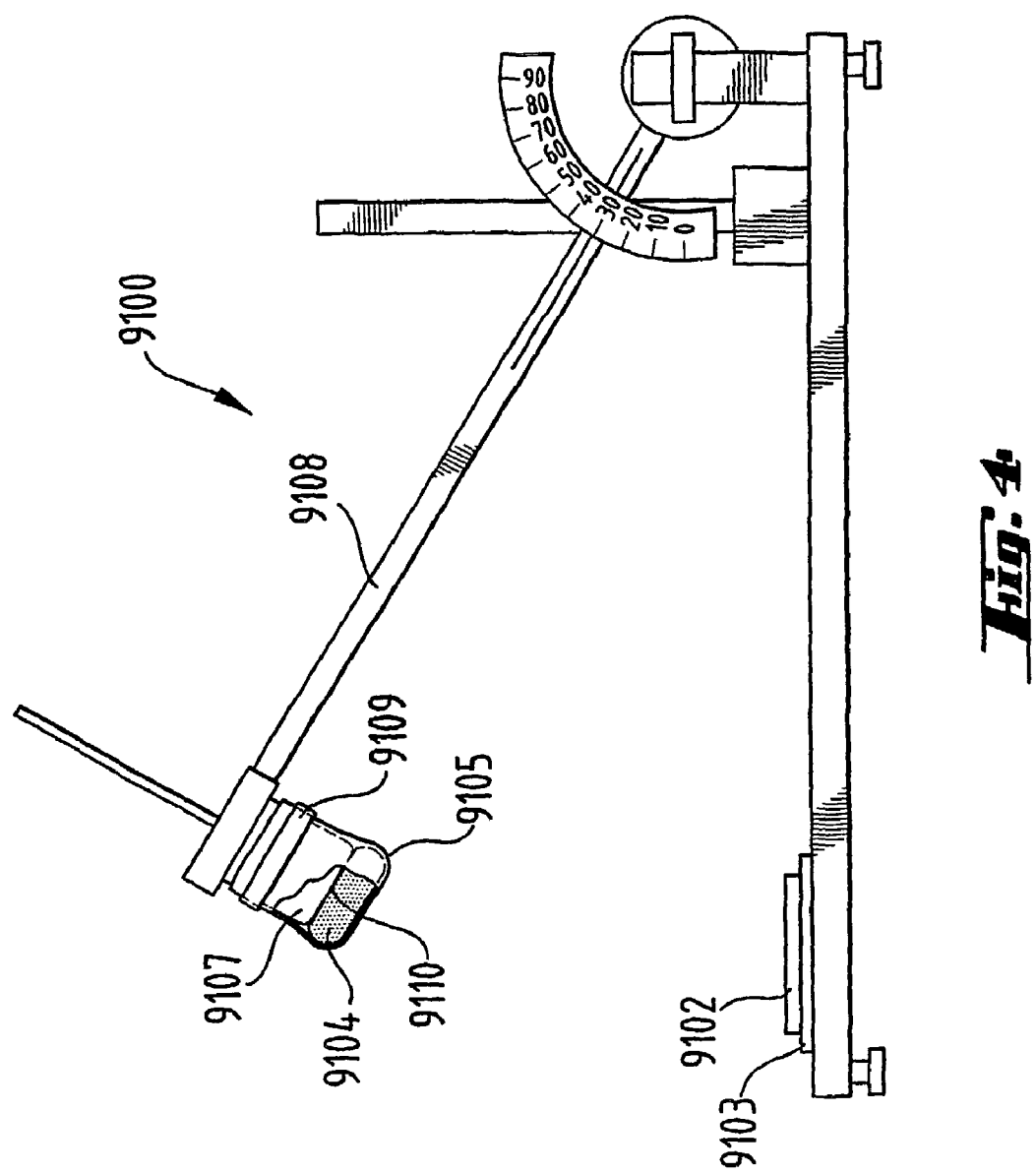

DISPOSABLE ABSORBENT ARTICLES HAVING LOW REWET AND A REDUCED EVAPORATION FROM THE CORE THROUGH THE TOPSHEET

CROSS REFERENCE

This is a continuation of International Application PCT/US00/17083, filed on Jun. 21, 2000.

FIELD OF INVENTION

The present invention relates to disposable absorbent articles, such as baby diapers, adult incontinence article, and the like. In particular, it aims at articles intended to receive large amounts of liquids, but still maintain good dryness conditions for the skin of the wearer.

BACKGROUND

Disposable, absorbent articles such as diapers, incontinence articles, sanitary towels, training pants and the like are well know in the art. Typically, disposable absorbent articles comprise a liquid pervious topsheet that faces the wearers body, a liquid impervious backsheet that faces the wearers clothing, and an absorbent core interposed between the liquid previous topsheet and the backsheet. The absorbent core must often be capable of absorbing and handling relatively large volumes of fluid like urine or other exudates discharged from the body of the wearer, and especially relatively large fluid volumes discharged over relatively short periods of time.

EP-A-0 774,242 discloses an absorbent article, having an uppermost (topsheet) material layer, which is directed towards the wearer's skin, and which is drained very effectively by an underlying acquisition/distribution region, such that a minimum of loosely bound liquid should remain in this layer in the topsheet.

It is also well known, to design articles, wherein the liquid barrier materials, often referred to as "backsheet" are gas or vapor permeable, thus allowing moisture to escape.

For applications, where the absorbency requirements are relatively minor, such as in so-called "panty-liner" products, non-woven or apertured polymeric film materials are often utilized as backsheets. For higher liquid loading, such as for baby diapers, microporous films, or so-called monolithic films are often preferred. Also known are various combinations fibrous layers with coating, films or the like.

Such breathable materials can be various kinds of webs, such as films which were rendered air/vapor permeable by aperturing as described in U.S. Pat. No. 5,628,737, or by exploiting the "microporosity" property as described in EP-A-0,238,200; EP-A-0,288,021; EP-A-0,352,802; EP-A-0,515,501; U.S. Pat. No. 4,713,068, whereby small voids are created within the film similar to very small cracks. WO 94/23107; WO 94/28224; U.S. Pat. No. 4,758,239; EP-A-0,315,013 all describe alternative breathable materials which can be fibrous textile or non-woven webs, with air/vapor easily penetrating through the relatively large pores of the structure. Such webs can be either untreated or treated with regard to improving their liquid impermeability properties, such as described in EP-A-0,196,654. In WO 95/16562 a laminate of a non-woven and a breathable film is disclosed. Further disclosures such as in WO 95/16746 relate to other materials allowing water molecules to diffuse through. Also, combinations of various materials comprising various layers any of the above elements are also well known.

The article should further be designed to retain not only the liquid discharged thereto, but also should provide a dry microclimate within the article, i.e. in the gas filled space between the article and the wearer.

PCT publication WO 98/58609 (Herrlein) discloses an article with a non-woven backsheet, wherein a dry micro climate is improved by using relatively high amounts of absorbent material, such as the so-called superabsorbent materials, when compared to the design capacity, i.e. the capacity to which the article is designed for the intended use.

A series of related and co-filed PCT applications (WO 00/10497; WO 00/10498, WO 00/104099, WO 00/10500, WO 00/10501) relates to breathable absorbent articles, including these being in the wet state. One approach described therein relates to creation of high permeability zones within an absorbent core, such as by aperturing the absorbent core, or by creating portions in the core containing substantially less high absorbency material than other portions of the core. Overall, the gas transfer mechanisms rely on gas diffusion mechanism, such as demonstrated by the preferred use of microporous film materials, as well as by the Tracer Gas Test.

However, there is still a need to provide absorbent articles with even further reduced tendency to create an undesirable high moisture content or relative humidity in the gas phase in the vicinity of the skin of the wearer, without compromising the liquid handling performance characteristics of the article, especially the acquisition and distribution properties.

SUMMARY

Henceforth, the present invention provides an absorbent article, having a topsheet, a backsheet and an absorbent core positioned therebetween. The absorbent core is composed of at least two substructures, namely the ultimate liquid storage core, and a liquid acquisition/distribution member positioned between the storage core and the topsheet. The acquisition/distribution member further includes an evaporation barrier such that the article exhibits a reduced level of liquid evaporating through its topsheet, as assessed by the Evaporation test described hereinafter. The article further exhibits a reduced tendency for rewetting, such as wetting the skin of the wearer during use.

A preferred way to achieve such low evaporation values is by including a barrier layer in the acquisition/distribution member, which is constructed to allow readily liquid passing through in the direction towards the ultimate storage core, but reduces the tendency of moisture passing therethrough in the opposite direction, i.e. in the direction towards the topsheet of the article, respectively towards the wearer oriented surface of the article.

In a particular embodiment, the invention is an apertured film, which is positioned within the acquisition/distribution materials, such as between two adjacent layers, which—apart from the apertured film therebetween—would be in direct contact with each other.

BRIEF DESCRIPTION OF DRAWINGS

FIG. 4: Schematic diagram of the Dynamic Fluid Transmission test set up.

DETAILED DESCRIPTION

As used herein, the term "absorbent articles" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

An absorbent article generally comprises
  an absorbent core (which may consist of sub-structures), and include the Acquisition/distribution member according to the present invention;
  a fluid pervious topsheet;
  a fluid impervious backsheet;
  optionally further features like closure elements or elastification.

Figure 1:
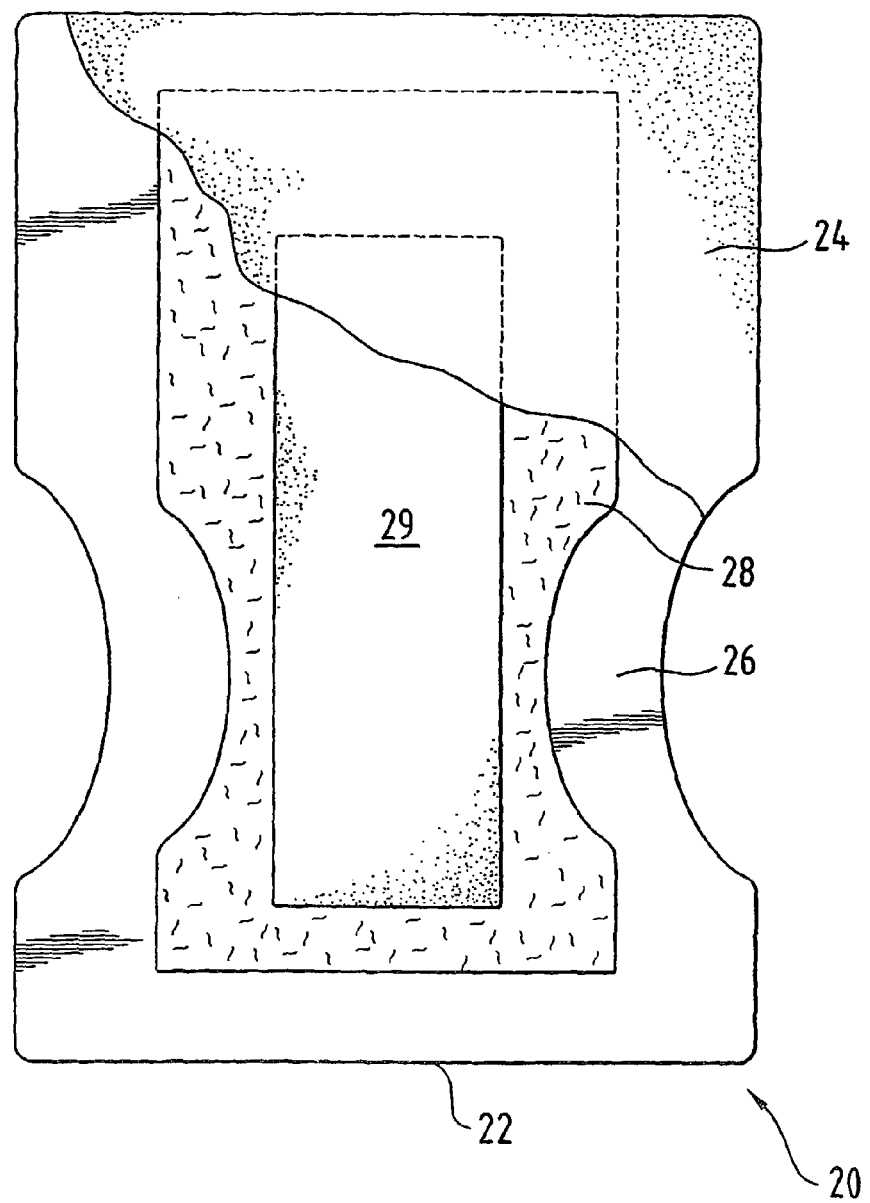
FIG. 1: Schematic diagram of an exemplary article.

A specific embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Primarily the invention relates to the use in disposable articles with high requirements for fluid acquisition, i.e. for uses where relatively high fluid volumes at relatively high flow rates need to be absorbed, such as for disposable baby diapers, articles for severely incontinent adults, training pants and the like. However, the invention can accordingly be applied to devices with relatively lower fluid rates and volumes, such as feminine hygiene devices or articles for light or moderately incontinent adults.

FIG. 1 is a plan view of the diaper 20 in its flat-out, uncontracted state (i.e. with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26.

If not specified differently, the term "upper" refers to the part of a structure directed towards the wearer of the article, "lower" directs away from the wearer.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 22 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,221,274 "Absorbent Article With Dynamic Elastic Waist Feature Having A Predisposed Resilient Flexural Hinge", Kenneth B. Buell.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The backsheet 26 can be manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bed-sheets and undergarments. The backsheet 26 may thus comprise a woven or nonwoven material, polymeric films such as thermoplastic films of polyethylene or polypropylene, or composite materials such as a film-coated nonwoven material. Conventionally, the backsheet is a thermoplastic film having a thickness of from about 0.012 mm to about 0.051 mm, such as RR8220 blown films and RR5475 cast films as manufactured by Tredegar Industries, Inc. of Terre Haute, Ind., US. The backsheet 26 is preferably embossed and/or matte finished to provide a more clothlike appearance.

The present invention is particularly suitable for being combined with breathable backsheets 26, which allow moisture transfer and in particular in the vapour phase from the article to the outside, in particular to the outside—i.e. away from the wearer.

However, such materials, whilst being vapour permeable, are preferably not liquid permeable so as to not unduly wet the exterior of the article. This can be best assessed by the polyhole rewet test as described hereinbelow. I has been found that consumer perceive articles exhibiting a value of more than 0.3 g as unpleasant. Henceforth, preferred articles comprise a backsheet material exhibiting a polyhole rewet of less than 0.3 g, preferably less than 0.2 g.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

Generally, the topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like.

Optionally, in addition to the described functional elements of the absorbent article, this may include further elements, as well known in the art, such as shown in EP-A-0, 254,476 (Alemany), with a non-limiting list being as follows:

a) Various cuff elements, such as leg-cuffs or so-called barrier cuffs with respective elastication;

b) Various fixations means, such as adhesive means such as tapes or so called panty fastening means, or mechanical fastening means, or combinations thereof. Alternatively, such articles can have topical adhesives, or can be hold in place by separate fixation means, such as panties or underwear, or specific fixation pants, such as so called stretch pants. The article can be a closeable, and optionally re-closeable structure, or can be full closure pant type article, optionally with openable or re-closeable seams.

c) Various feces handling means, such as topsheets having large apertures designed to be aligned with the anal opening, or feces receiving means, which can underlay a topsheet, whereby the latter preferably comprises a multitude of apertures.

For this embodiment, care should be taken to not arrange the feces handling regions to impede the urine handling regions, if the absorbent article is intended to receive both kinds of exudates.

d) Other elements of the article can include elastication means, such as stretchable regions to allow more comfortable size and fit adjustment, such panels can be arranged in the regions of the fixations elements of the article, or in the tapes, or in the waist regions.

The Liquid Storage Core

The ultimate storage core useful for the present invention can be any structure providing sufficient ultimate storage capacity for the intended use, such as well known structures comprising so-called superabsorbent materials, optionally, and often preferably in combination with fibrous materials, such as cellulose fluff and/or synthetic fiber materials, see, for example EP-A-0,774,242; PCT applications IB99/00739, IB99/00741, IB99/00751, all filed on Apr. 23, 1999; PCT Application US98/105044, filed on Mar. 18, 1998.

The storage core may comprise polymeric porous materials, preferably made by the High Internal Phase Emulsion Polymerization process ("HIPE" foams), such as described in PCT applications IB99/00404 and IB99/00408, both filed Mar. 12, 1999. All these publications are incorporated herein by reference.

Optionally, and often preferred, the storage core can be enveloped by a suitable web, such as a paper tissue or a suitable non-woven material, such as described in WO 97/07761 and in PCT application IB99/00689, filed on Apr. 16, 1999, which is incorporated herein by reference.

Preferably, storage cores allow for convective air or gas flow therethrough by exhibiting a permeance (i.e. air or gas permeability related to the thickness) of more than 0.1 Darcy/mm, preferably more then 1.0 Darcy/mm, such as described in co-filed PCT application PCT/US00/17084, which is incorporated herein by reference.

In combination with respective caliper measurements (on the dry and/or wet article, respectively), the permeance of the structure can be calculated, by dividing the permeability by the thickness of the structure. For inhomogeneous structures, the sample preparation or the test setup might require adaptation so as to not measure through the "venting channels" such as apertures and/or low basis weight, and/or low basis capacity regions. Preferably, an article according to the present invention provides for wet permeance of more than about 0.1 Darcy/mm, preferably more than about 0.5 Darcy/mm, and even more preferably more than about 1.0 Darcy/mm. Typically, the respective dry article permeance is less than the permeance of the wetted article.

The Acquisition/Distribution System

In order to facilitate liquid entering the absorbent core, an acquisition/distribution member or system 29 is positioned between the storage core and the topsheet, at least in the liquid discharge region.

In EP-A-0,774,242 such regions are described, which can be dual layered structures, such as made from modified cellulosic materials combined with a synthetic non-woven material.

The Barrier Layer

An essential element of the present invention is a barrier functionality included within the acquisition/distribution system. The barrier functionality should enable the liquid to penetrate therethrough as readily and unimpeded as possible in the direction away from the wearer.

It should further minimize the evaporation of moisture from the article as much as possible.

Without wishing to be bound by the theory, it is believed, that the particular benefits of such layers are caused by two effects, namely the minimization of liquid being back-transferred to the diaper surface from the inner regions of the article upon drying of the surface. It is further believed, that also vapor phase transfer from the inner parts of the article to the surface is reduced by effective barrier functionality.

Depending on the exact configuration of this system, this barrier functionality can be arranged at the surface of the acquisition/distribution system towards the storage core or towards the topsheet, or can be integrally positioned within the system, such as between two layers of the system.

This barrier should be positioned upwardly, i.e. towards the wearer during the intended use, of this element of the system, which is most prone for retaining higher amounts of free liquid (i.e. liquid with a low desorption pressure, as defined in above mentioned PCT application IB99/00751, which is incorporated herein by reference).

When for example considering a composite consisting of the modified cellulosic material and the nonwoven web as described an EP-A-774,242, the preferred positioning is between these two layers.

The barrier functionality should be positioned at least in these regions of the article, where the loading occurs, and further, where such materials having a propensity for readily releasing free liquid are close to the surface materials of the article.

Following the above, the barrier functionality can be suitably achieved by a relatively thin layer, such as an apertured polymeric film such as polyethylene or polypropylene, both optionally hydrophilized, of a typical basis weight of more than about 5 gsm or less than about 50 gsm, preferably of more than about 10 gsm or less than about 25 gsm.

The apertures can have an individual open area of from 1.4 mm2 to 3.0 mm2 and preferably from 1.5 mm2 to 2.5 mm2. The total open area of these apertures in the barrier layer should be in the range from 5% to 30%, preferably from 10% to 20% of the surface area of the barrier layer.

Preferred embodiments include materials with a preferential liquid handling directionality, such as apertures films, as known to be used as topsheet or backsheet materials in absorbent articles, and particularly preferred embodiments comprise a resilient, three dimensional web which consists of a liquid impervious polymeric film having apertures.

Suitable materials are described—albeit for backsheet or topsheet materials respectively—PCT applications US99/02395 and US99/02393, both filed on Feb. 3, 1999, which are incorporated herein by reference.

Such webs are oriented such that the larger diameter of the apertures is positioned upwardly, i.e. oriented towards the wearer, and the smaller openings in the direction towards the storage core. During use, the funneling effect of the narrowing capillaries in combination with a valve effect upon pressure application provide the directionality of the liquid penetration.

In a particular embodiment, the apertures of the formed films have varying sizes, such as described in EP-A-0,749,738 for a topsheet application. Thus they have apertures which herein are referred to as "large apertures" and apertures which herein are referred to as "small apertures".

For all measurements regarding the size of the apertures, the plane of the smallest cross sectional areas of the aperture should be used, such as can be determined by optical analysis.

The large apertures have an individual open area of from 1.4 mm2 to 3.0 mm2 and preferably from 1.5 mm2 to 2.5 mm2. The total open area of the large apertures in the barrier layer should be in the range from 5% to 20%, preferably from 10% to 20% of the surface area of the barrier layer.

The small apertures of this preferred embodiment of the barrier layer of the absorbent article have an individual open area of less than 1.4 mm2 and typically not smaller than 0.15 mm2 Apertures which are even smaller are usually not suitable for liquid transport and would only function as gas permeable apertures. Preferably, the optional small apertures are in the range of 0.25 mm2 to 0.4 mm2.

The apertures are preferably substantially circular or polygonal. Their shape is limited by having a ratio of the largest to the smallest inner diagonal length in the range between 1 and 6, preferably 1 and 3. The total open area of all liquid transport apertures in the barrier layer is in the range of 10% to 40%, preferably 15% to 35% of the total area of the barrier layer.

Optionally, the barrier layer can have macro apertures, such as an aperture of significantly larger size than the above mentioned ones, such as to allow higher viscous materials or even solid materials, such as feces, to pass through.

In a particular embodiment, an apertured films, such as a dual aperture size formed film, is sandwiched between two porous structures, preferably fibrous structures, such that the layer underneath the apertured film has a low liquid holding ability, and preferably comprises chemically modified cellulose, and the layer on top of the apertured film, i.e. oriented towards the wearer, is a hydrophilized nonwoven web, such as a PET web bonded by hydrophilic resin. The chemically treated stiffened cellulosic material (CS) supplied by Weyerhaeuser Co., US under the trade designation of CMC can be airlaid into a web of about 0.08 g/cm3 density at a basis weight of about 280 gsm; high-loft chemically bonded nonwoven {FT} PET web can be supplied by FIBERTECH, North America under the designation type 6852, a chemically bonded PET fibre web of a basis weight of 43 g/m2.

The acquisition/distribution system can be formed by first air-forming the cross-linked cellulosic pad, over-laying it by a dual aperture such as available from BP Chemicals under the designation 45105 with the smaller openings towards this layer, and further overlaying it by the resinbonded PET web.

When considering the manufacturing of absorbent articles, such barrier composite materials can be formed "on-line", i.e. directly and integral with the manufacturing process of the article, or can be formed "off-line", i.e. not at the article production line, with an additional storage step, such as on rolls or in boxes, between the making of the barrier layer and the article.

Such barrier layers provide improvements with regard to the reduction of the moisture transfer from the article, and in particular from the acquisition/distribution regions to the vapour phase outside pf the article, i.e. to the space between the article and the skin of the wearer during the intended use.

Henceforth, a suitable article comprising such a barrier layer reduces—when submitted to the evaporation test as described hereinafter—by at least 25%, preferably more than 30%, and even more preferably more than 50% compared to an equivalent design except for not having such a barrier layer.

Preferably, a suitable article provides an evaporation rate of less than 150 g/m2/hr, preferably of less than about 120 g/m2/hr, and even more preferably of less than about 100 g/m2/hr Examples A conventional baby diaper PAMPERS BabyDry Maxi size (i.e. for babies of 9 to 18 kg) such as produced and sold by Procter & Gamble in Germany, has been used as a comparative example, and has further been modified by inserting the above referred to a apertured formed film material as available from BP Chemicals under the designation 45105 between the first layer of the acquisition/distribution element, and the second layer thereof, such that the smaller opening of the formed film are directed towards the storage core.

Submitting the product to the Evaporation test as described hereinafter at a load of 10 ml per sample specimen, an area specific evaporation rate of about 100 g/m2/hr result, as compared to the same product design except the apertured formed film layer, showing an evaporation rate of about 150 g/m2/hr.

Test Procedures

Evaporation Rate from Loaded Diaper Core

This test method relates to an absorbent article. A rectangular test specimen of 70 mm (in transverse direction of the article) by 100 mm (in longitudinal direction of the article) is cut by suitable scissors or a cutting blade from a representative part of the absorbent core, such as transversely centered, and from about 6 cm from front core edge.

The dry weight is recorded, and the specimen is placed in a glass box of about 72 mm by 102 mm, and about 40 mm high without lid, with backsheet down, and the topsheet facing to environment. The specimen is loaded with 10 g of 0.9% saline solution per gram test specimen, whereby the liquid is evenly distributed over the area, thereby avoiding the wetting of the glass box.

The complete weight of the glass box with the loaded specimen is recorded.

The equipment is placed into a climate chamber such as available from WTB Binder, Tuttlingen, Germany, type 37720099003100 at 33° C.+/−2°, at 50% relative humidity (RH)+/−3%. The ventilation is adjusted to provide an air flow velocity of about 15 cm/sec over the opening of the glass box.

After two hours evaporation time, the end weight of the complete glass box with the specimen is recorded.

The area specific evaporation rate is determined

Evaporation Rate=(Start weight−End weight)/(Time× sample area).

whereby the start and end weight is the total weight of the glass box with the specimen.

The above loading values have been found useful for baby diapers, especially for baby diapers for babies of the size of about 9 to 18 kg, often referred to as MAXI size. In case of very different absorbent capacities of the absorbent article under consideration, the amount of liquid load should be adjusted to about 50% of the theoretical basis capacity as defined hereinafter.

Design Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual toddlers. Another user group may be larger children, still suffering from a certain form of incontinence. Also, incontinent adults can use such articles, again with a wide range of loading conditions, generally referred to as light incontinence ranging up to severe incontinence.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. If the processes under consideration have asymptotic kinetic behavior, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

In case of applying the present invention to other articles requiring different end-uses, one skilled in the art will be able to readily adopt the appropriate design capacities for other intended user groups.

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers can be used for such materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

With such definitions, for example a so-called "panty liner" product exhibits very low Ultimate storage capacities of a few ml or less. Feminine Hygiene pads have often up to about 20 ml, light urinary incontinence articles have for example 75 ml or about 90 ml, medium urinary incontinence articles, or also smaller baby diaper can have about 165 ml, and toddler size baby diapers reaching 300 ml or more, and severe adult incontinence article having 600 ml or more of ultimate storage capacity.

Teabag Centrifuge Capacity Test (TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately.

After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilized at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)]÷(dry absorbent material weight).

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cutouts can be used to determine a "basis capacity" (i.e. the amount of capacity contained in a unit area of the specific region of the article. Depending on the size of the unit area (preferably 2 cm by 2 cm) the defines how much averaging is taking place—naturally, the smaller the size, the less averaging will occur.

Ultimate Storage Capacity

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers (SAP) can be used for such SAP materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

Acquisition Test

This test should be carried out at about 22+/−2° C. and at 35+/−15% relative humidity.

The synthetic urine used in these test methods is 0.9% saline solution.

Figure 2:
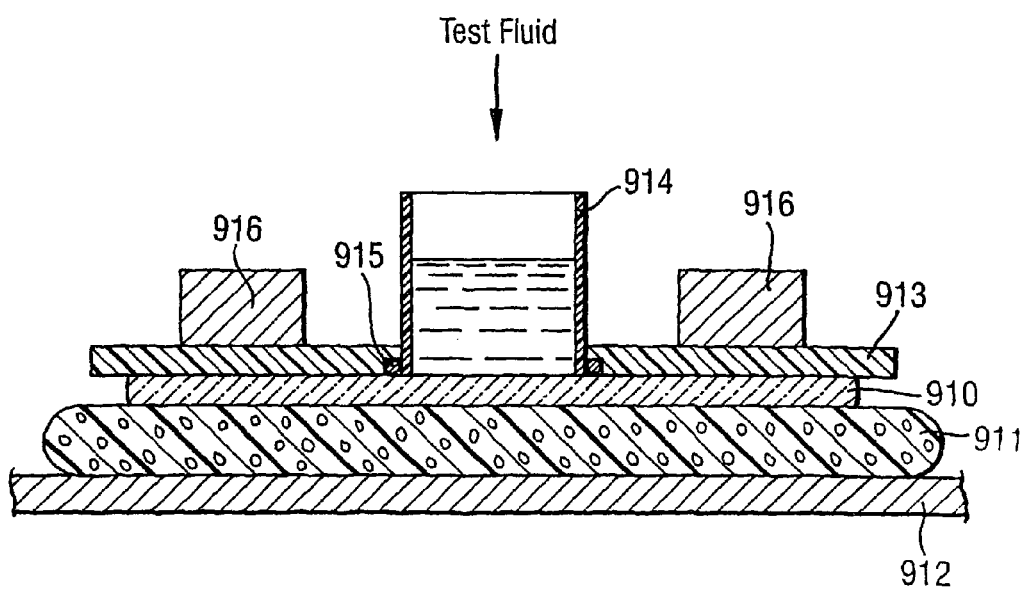
FIG. 2: Schematic diagram of Acquisition test set up.

Referring to FIG. 2, an absorbent structure 910 is loaded with a 75 ml gush of synthetic urine at a rate of 15 ml/s using a pump (such as Model 7520-00, supplied by Cole Parmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 911 within a perspex box (only base 912 of which is shown). A perspex plate 913 having a 5 cm diameter opening in its middle is placed on top of the sample on the loading zone of the structure. Synthetic urine is introduced to the sample through a cylinder 914 fitted, and glued into the opening. Electrodes 915 are located on the lowest surface of the plate, in contact with the surface of the absorbent structure 910. The electrodes are connected to the timer. Loads 916 are placed on top of the plate to simulate, for example a baby's weight. A pressure of about 50 g/cm2 (0.7 psi) is achieved by positioning weights 916, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products or for smaller babies), the settings in particular of the fluid volume per gush should be adjusted appropriately to about 20% of the total article design capacity, and the deviation from the standard test protocol should be recorded.

Figure 3:
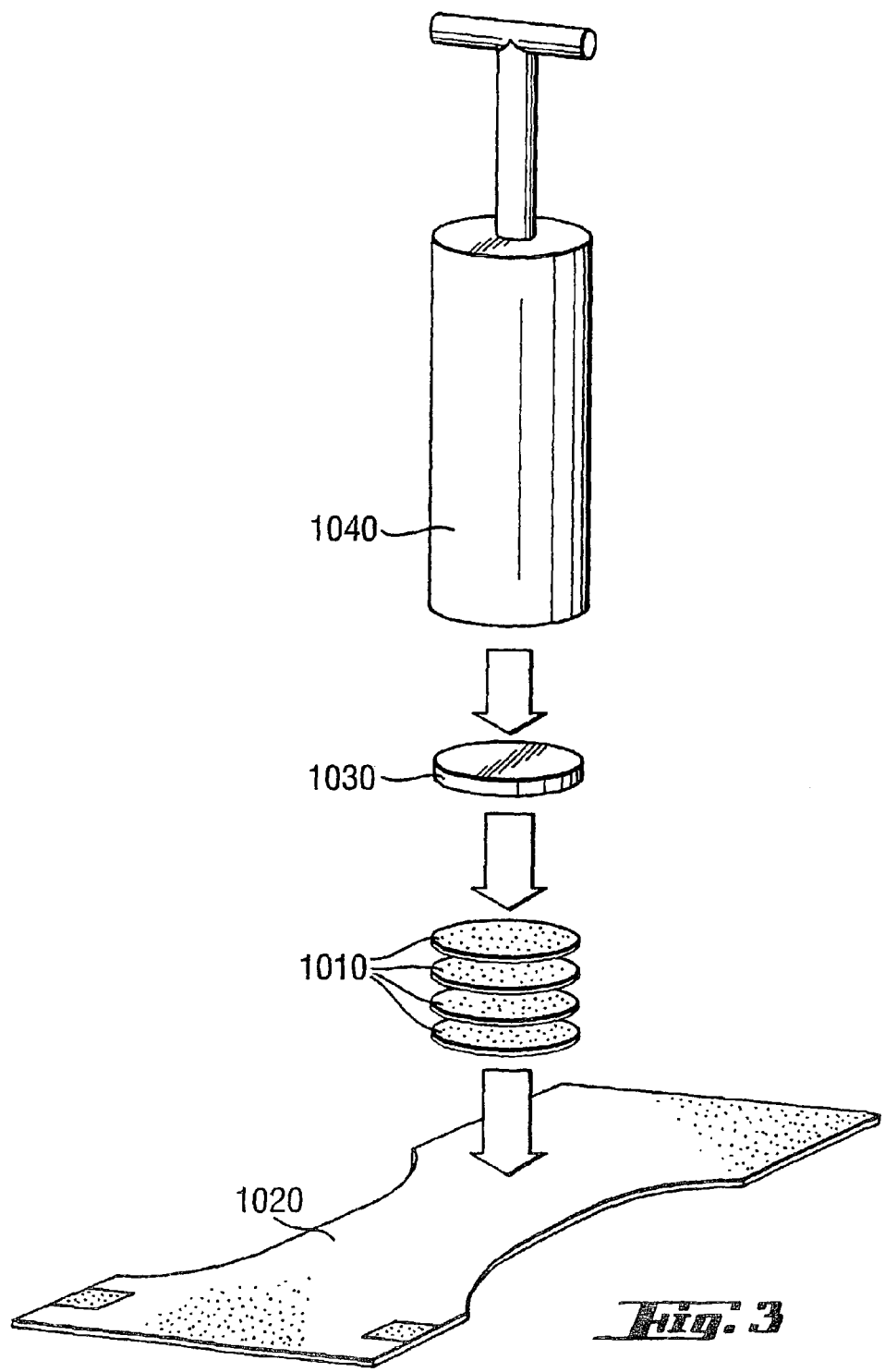
FIG. 3: Schematic diagram of the Post Acquisition Collagen Rewet test set up.

Post Acquisition Collagen Rewet Method (Refer to FIG. 3)

Before executing the test, the collagen film as purchased from NATURIN GmbH, Weinhein, Germany, under the designation of COFFI (or equivalent) and at a basis weight of about 28 g/m2 is prepared by being cut into sheets of 90 mm diameter e.g. by using a sample cutter device, and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample 1020 is carefully placed flat on a lab bench.

4 sheets of the precut and equilibrated collagen material 1010 are weighed with at least one milligram accuracy, and then positioned centered onto the loading point of the article, and covered by perspex plate 1030 of 90 mm diameter, and about 20 mm thickness. A weight 1040 of 15 kg is carefully added (also centred). After 30+/−2 seconds the weight and perspex plate are carefully removed again, and the collagen films are reweighed.

The Post Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimising these identified relevant parameter such as in a designed experiment according to standard statistical methods with realistic in use boundary conditions.

Caliper Measurement Method

The intent of this method is to provide a procedure to determine the thickness of the absorbent article at the crotch point and in either of the waist regions immediately adjacent the crotch region. The test can be executed with a conventional caliper gauge, such as Type EG-225 available from ONO SOKKI Technology Inc. III. US, with an appropriate gauge stand, having an aluminium circular sample foot of 41 mm diameter, having a weight of foot of 10 g. An additional weight is added to achieve a total of 160 g to adjust the pressure to 1.18 kPa (0.173 psi).

Topsheet-on-Acquisition-Material-Wetness Test

This test is used to evaluate the topsheet performance when it is combined not only with a "standard core", but also with an acquisition material.

Three pieces of the "Core replacement" filter paper supplied by Hollingsworth & Vose, UK of the type ERT FF3.W/S of 30.5 cm by 14.0 cm are put underneath a layer of acquisition/distribution material as described in the Example of 18 cm by 12 cm. The topsheet sample of also 18 cm by 12 cm is placed upon this.

Then 40 ml of test fluid (0.9% saline solution) (if necessary adjusted for the loading factor of the core replacement filter paper) are added at a rate which avoids overflow of the fluid at the sides of the sample.

A weight of 3.642 kg (8 lbs) is added carefully.

After 15 minutes, the weight increase of the topsheet (after pre-weighing it in the dry state) is measured.

Topsheet-Finished-Product-Wetness Test—Finished Product

After executing the above described Finished-Product-Acquisition test, the topsheet is carefully removed (preferably as complete as possible) from the rest of the product. It is then placed between preweighed pick-up filter paper (supplied by Hollingsworth & Vose, UK, under the designation MEDIUM WHITE W/S) of 7 cm by 10 cm, with 2 sheets underneath and 2 sheets above and a weight of 7.5 kg (on the same area as the filter paper) is added.

After 30 secs the filter paper has drained the topsheet practically quantitatively, and the fluid retained in the topsheet (wetness) can be measured by re-weighing the filter i.e. paper and determining the difference.

Dynamic Fluid Transmission Test

Dynamic Fluid Transmission is measured with the apparatus 9100 shown in FIG. 4. According to this test, an absorption material 9102 weighed to the nearest 0.0001 gram is placed directly on top of the energy absorbing impact pad 9103. The absorption material 9102 may comprise a No. 2 filter paper available from Whatman Laboratory Division, Distributed by VWR Scientific of Cleveland, Ohio. The absorption material should be able to absorb and retain simulated urine which passes through the sheet material being tested. The energy absorbing impact pad 9103 is a carbon black filled cross linked rubber foam. The 12.7 cm by 12.7 cm (5 inch by 5 inch) square impact pad has a density of 0.1132 g/cm3 and a thickness of 0.79 cm (0.3125 inches). The impact pad 9103 has a Durometer Value of A/30/15 according to ASTM 2240-91. A circular absorbent core material 9104 measuring 0.0635 meters (2.5 inches) in diameter is weighed. The absorbent core material may comprise individualized, crosslinked wood pulp cellulosic fibers as described in U.S. Pat. No. 5,137,537 issued to Herron et al. on Aug. 11, 1992.

Other absorbent materials that can be used include airfelt, tissue, cellulose wadding, as long as these exhibit the required absorbent capacity of at least 10 g/g. If the materials have a capacity below 10 g/g then they should be wetted to at least 80% of their saturation capacity. Also, the absorbent materials should be essentially free of "superabsorbent materials" which might bind the liquid too tightly and thus affect the results.

The absorbent core material should be able to hold a sufficient amount of simulated urine, e.g., at least about ten times its dry weight. The absorbent core has a basis weight of about 228 g/m2. The absorbent core material is then is loaded with simulated urine to about ten (10) times its dry weight. The simulated urine is 0.9% saline solution.

A section of the backsheet material 9105 to be tested is placed face down with the outside surface on a clean and dry tabletop. The loaded core material 9104 is placed directly in the center of the backsheet material 9105. The backsheet/core arrangement is then secured to the impact portion 9107 of the impact arm 9108 with a rubber band 9109. The backsheet/core arrangement is positioned such that the core 9104 is adjacent the bottom surface 9110 of the impact portion 9107. The impact arm 9108 is raised to a desired impact angle to provide the desired impact energy. The impact arm 9108 is dropped and the impact arm 9108 is then allowed to rest on the sample for about 10 seconds after impact. The arm is then raised and the filter paper 9102 is removed and placed on a digital scale. The mass of the wet filter paper is then recorded at the three minute mark. The dynamic fluid transmission value (DFTV) is calculated and expressed in g/m2 using the following formula:

DFTV=mass of the wet filter paper (grams)−mass of the dry filter paper (grams) impact area ($m2$)

The impact area, expressed in m2, is the area of the bottom surface 9110 of the impact portion 9107. The impact area is 0.00317 m2. The absorbent core material 9104 should have an area slightly larger than that of the impact area of the surface 9110.

What is claimed is:

1. An absorbent article comprising a topsheet, a backsheet, and an absorbent core interposed between said topsheet and said backsheet, said absorbent article having a periphery, said topsheet and said backsheet extending laterally and longitudinally beyond said absorbent core, thereby surrounding said absorbent core and forming said periphery of said absorbent article, said absorbent core comprising a liquid storage region and a liquid acquisition/distribution region positioned between said liquid storage region and said topsheet, said acquisition/distribution region comprising a first acquisition/distribution layer and a second acquisition/distribution layer with a liquid permeable evaporation barrier layer disposed between said first and said second acquisition/distribution layers, said second acquisition/distribution layer being positioned between the liquid storage region and the evaporation barrier, said barrier layer comprising a film material including a first plurality of apertures having individual open areas of more than about 1.4 mm$^2$ and less than about 3.0 mm$^2$ and a second plurality of apertures having a mean aperture size smaller than a mean aperture size of said first plurality of apertures, wherein said article provides an area specific evaporation rate of less than 150 g/m$^2$/hr when submitted to the disclosed Evaporation Rate test.

2. Absorbent article according to claim 1, said second plurality of apertures having individual open areas of less than about 1.4 mm$^2$.

3. Absorbent article according to claim 1, wherein said acquisition/distribution region comprises chemically stiffened cellulosic fibers.

4. Absorbent article according to claim 1, wherein said acquisition/distribution region comprises a resin bonded carded PET web.

5. Absorbent article according to claim 1, exhibiting a post acquisition collagen rewet value of less than 100 mg.

6. Absorbent article according to claim 1, wherein said backsheet is water vapour permeable and exhibits a dynamic fluid transmission value of less than 0.3 g/m$^2$.

7. Absorbent article according to claim 1, wherein said backsheet is selected to provide a dynamic fluid transmission value of less than 100 g/m$^2$.

8. Absorbent article according to claim 1, wherein said article is permeable for convective gas transport even when wetted, and provides a wetted permeance of more than 0.1 Darcy/mm.

* * * * *